(12) United States Patent
Piotrowski et al.

(10) Patent No.: US 9,994,584 B2
(45) Date of Patent: Jun. 12, 2018

(54) PROCESS OF SYNTHESIZING 3-(4-METHYLPIPERAZINE-1-CARBONYL)-7-OXABICYCLO[2.2.1]HEPTANE-2-CARBOXYLIC ACID

(71) Applicant: LIXTE BIOTECHNOLOGY, INC., East Setauket, NY (US)

(72) Inventors: Jason J. Piotrowski, Ypsilanti, MI (US); Dumitru Ionescu, Ann Arbor, MI (US)

(73) Assignee: Lixte Biotechnology, Inc., Setauket, NY (US)

( * ) Notice: Subject to any disclaimer, the term of this patent is extended or adjusted under 35 U.S.C. 154(b) by 0 days. days.

(21) Appl. No.: 15/518,282

(22) PCT Filed: Oct. 14, 2015

(86) PCT No.: PCT/US2015/055485
§ 371 (c)(1),
(2) Date: Apr. 11, 2017

(87) PCT Pub. No.: WO2016/061193
PCT Pub. Date: Apr. 21, 2016

(65) Prior Publication Data
US 2017/0305925 A1    Oct. 26, 2017

Related U.S. Application Data

(60) Provisional application No. 62/064,249, filed on Oct. 15, 2014.

(51) Int. Cl.
| | |
|---|---|
| *C07D 493/08* | (2006.01) |
| *C07D 247/00* | (2006.01) |
| *C07D 405/12* | (2006.01) |
| *A61K 31/496* | (2006.01) |

(52) U.S. Cl.
CPC .......... *C07D 493/08* (2013.01); *A61K 31/496* (2013.01); *C07D 247/00* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 2013/0302402 A1 | 11/2013 | Kovach | |
| 2014/0088091 A1* | 3/2014 | El-Azab | C07D 513/04 514/221 |

FOREIGN PATENT DOCUMENTS

EP    0 081 892 A2    6/1983

OTHER PUBLICATIONS

International Search Report in connection with PCT International Application No. PCT/US2015/055485.
Written Opinion of the International Searching Authority in connection with PCT International Application No. PCT/US2015/055485.

* cited by examiner

*Primary Examiner* — Emily Bernhardt
(74) *Attorney, Agent, or Firm* — Andrea L. C. Reid; Dechert LLP

(57) ABSTRACT

The present invention provides a process for producing the compound having the structure:

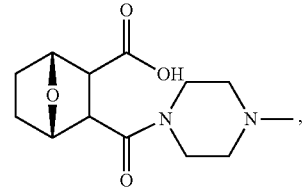

comprising
(a) reacting a compound having the structure:

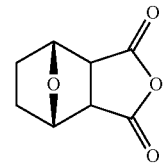

with a compound having the structure:

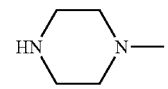

in the presence of a first organic solvent under conditions sufficient to produce the compound,
wherein the first organic solvent is a substituted benzene.

2 Claims, 3 Drawing Sheets

| Reaction Parameters and Operational Steps | | Process Schematic | In-process Test |
|---|---|---|---|
| 1. Reaction components | Add to 22-L flask: 6.2028 kg cumene 0.9027 kg (5.368 mol) norcantharidin 1.3349 kg cumene 1.6067 kg (16.041 mol, 3.0 mol eq.) N-methylpiperazine. | Norcantharidin $C_9H_8O_4$ 168.15 + N-methylpiperazine $C_5H_{12}N_2$ 100.16 | LB-100 is the only product crystallizing from the reaction mixture. |
| 2. Reaction temperature | Mix while heating to 90°C. | | |
| 3. Reaction time | Stir mixture for 21 hours at 85.1-97.1°C. | | |
| 4. Crystallization and isolation of crude product | Cool slurry to ambient temperature. | LB-100 crude product | |
| 5. Filtration and Isolation of final product | Isolate solids | | |
| 6. Wash step | Wash solids with cumene (1.1703 kg) and 3 times with acetone (1.1281 kg, 1.1617 kg, 1.1850 kg) | | |
| 7. Oven drying under vacuum | Dry solids at 80°C and under vacuum (28-30 mmHg) for 22 hours and 25 minutes. | | |
| 8. Package and yield determination | Weigh final product (1.3743 kg, 95.4% yield). | LB-100 $C_{13}H_{20}N_2O_4$ 268.31 | |

Fig. 1

PROCESS OF SYNTHESIZING 3-(4-METHYLPIPERAZINE-1-CARBONYL)-7-OXABICYCLO[2.2.1]HEPTANE-2-CARBOXYLIC ACID

CROSS-REFERENCE TO RELATED APPLICATIONS

This application is a § 371 national stage of PCT International Application No. PCT/US2015/055485, filed Oct. 14, 2015, claiming the benefit of U.S. Provisional Application No. 62/064,249, filed Oct. 15, 2014, the contents of each of which are hereby incorporated by reference into the application.

Throughout this application various publications are referenced. The disclosures of these documents in their entireties are hereby incorporated by reference into this application in order to more fully describe the state of the art to which this invention pertains.

BACKGROUND OF THE INVENTION

Protein phosphatase 2A (PP2A), a family of the major serine/threonine phosphatases in cells, is widely considered a tumor suppressor (Van Hoof, C. et al. 2004; Westermarck, J. et al. 2008). Inhibition of PP2A is thought to be a precursor of malignant transformation of human cells and some PP2A inhibitors such as okadaic acid are associated with tumorigenesis and tumor progression (Junttila, M. R. et al. 2007; Suganuma, M. et al. 1988), Structurally, PP2A has three subunits and each subunit has alternative isoforms (Mumby, M. 2007), resulting in over 60 heterotrimeric holoenzymes (Gwinn, D. et al. 2013). Because of the complicated constitutive and various signaling pathways involving PP2A, this ubiquitous phosphatase may play distinct roles in different tissue and disease states. For instance, the B55a regulatory subunit of PP2A was shown to enhance the survival of human fibrosarcoma cells during glutamine deprivation (Reid, M. A. et al. 2013), while inhibition of the B56γ subunit induces tumorigenic transformation of human embryonic kidney cells (Chen, W. et al. 2004), thereby acting like B56α as a tumor suppressor (Arnold, H. K. et al. 2008). This diversity of PP2A function in tumorigenesis suggests in certain circumstances targeting PP2A may be an effective cancer strategy.

Cantharidin, a natural product isolated from *Mylabris sidae*, and several cantharidin derivatives have PP2A inhibitory activity, and have been used as anti-cancer agents for decades (Hart, M. E. et al. 2004; Li, W. et al. 2010; Liu, D. et al. 2009; McCluskey, A. et al. 2000). The mechanism by which PP2A exerts anti-cancer activity is believed be abrogation of cell cycle checkpoints and induction of mitotic catastrophe (Kaley, P. et al. 2011). Although cantharadin has previously been used in the treatment of hepatomas and has shown efficacy against multidrug-resistant leukemia cell lines (Efferth, T. et al. 2002), its severe toxicity limits its clinical usefulness. LB100 is a small molecule derivative of cantharadin with significantly less toxicity. Previous preclinical studies have shown that LB100 can enhance the cytotoxic effects of temozolomide, doxorubicin, and radiation therapy against glioblastoma (GBM), metastatic pheochromocytoma, and pancreatic cancer (Wei, D. et al. 2013; Lu, J. et al. 2009; Zhang, C. et al. 2010b; Martiniova, L. et al. 2011). LB100 is also undergoing a phase 1 study in combination with docetaxel for the treatment of solid tumors (Chung, V. 2013).

SUMMARY OF THE INVENTION

The present invention provides a process for producing the compound having the structure:

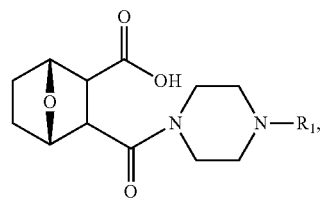

wherein $R_1$ is H, alkyl, alkenyl, alkynyl, heteroalkyl, hydroxyalkyl, aryl, heteroaryl, alkylaryl, alkylheteroaryl or C(O)Ot-Bu, comprising (a) reacting a compound having the structure:

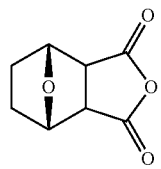 [SMILES: O=C1OC(=O)C2C1[C@@H]1CC[C@H]2O1]

with a compound having the structure:

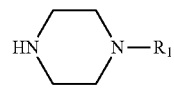

in the presence of a first organic solvent under conditions sufficient to produce the compound, wherein the first organic solvent is a substituted benzene.

The present invention provides a process for producing the compound having the structure:

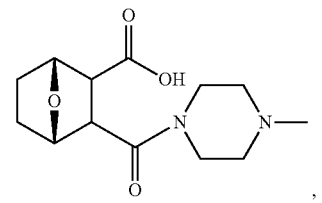 [SMILES: CN1CCN(C(=O)C2C(C(=O)O)[C@H]3CC[C@@H]2O3)CC1]

comprising
(a) reacting a compound having the structure:

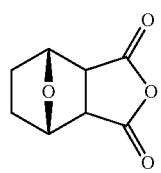 [SMILES: O=C1OC(=O)C2C1[C@@H]1CC[C@H]2O1]

with a compound having the structure:

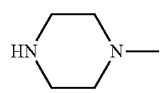

in the presence of a first organic solvent under conditions sufficient to produce the compound,
wherein the first organic solvent is a substituted benzene.

The present invention also provides a process for producing the compound having the structure:

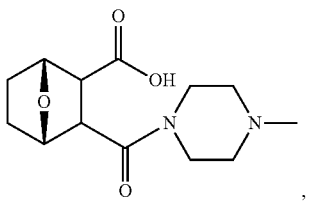 [SMILES: CN1CCN(C(=O)C2C(C(=O)O)[C@H]3CC[C@@H]2O3)CC1]

comprising
(a) adding a compound having the structure:

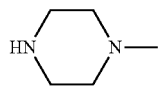

to a solution of a compound having the structure:

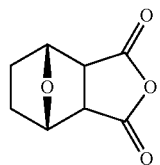

in isopropylbenzene;
(b) filtering the mixture of step (a) to obtain filtered solids;
(c) washing the filtered solids produced in step (b) with isopropylbenzene and acetone; and
(d) drying the washed solids produced in step (b) under vacuum.

The present invention also provides a process for producing the compound having the structure:

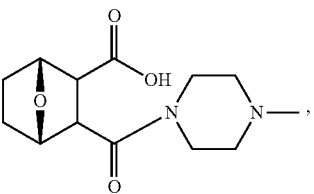 [SMILES: CN1CCN(C(=O)C2C(C(=O)O)[C@H]3CC[C@@H]2O3)CC1]

comprising
(a) adding a compound having the structure:

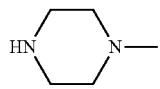

to a solution of a compound having the structure:

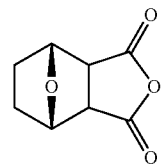 [SMILES: O=C1OC(=O)C2C1[C@@H]1CC[C@H]2O1]

in isopropylbenzene and stirring the solution for 16 to 29 hours at a temperature of 85 to 100° C.;
(b) filtering the mixture of step (a) to obtain filtered solids;
(c) washing the filtered solids produced in step (b) with isopropylbenzene and acetone; and
(d) drying the washed solids produced in step (c) under vacuum.

BRIEF DESCRIPTION OF THE FIGURES

FIG. 1: Detailed reaction parameters for synthesis of LB100 with cumene as solvent.
FIG. 2: Carbon NMR of LB100 obtained by the present method.

DETAILED DESCRIPTION OF THE INVENTION

Figure 2:
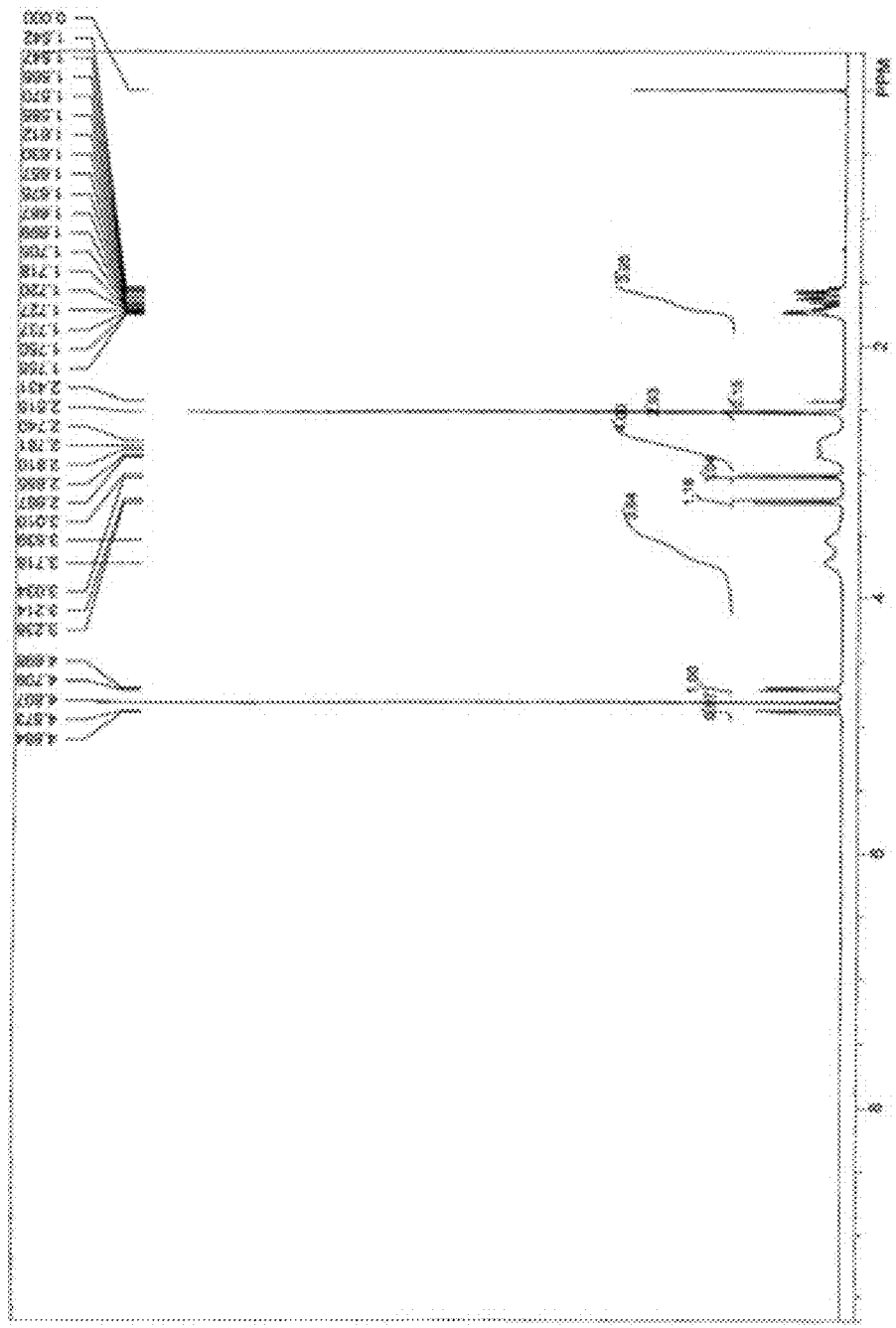
FIG. 2: Proton NMR of LB100 obtained by the present method.

The present invention provides a process for producing the compound having the structure:

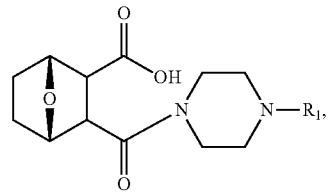

wherein $R_1$ is H, alkyl, alkenyl, alkynyl, heteroalkyl, hydroxyalkyl, aryl, heteroaryl, alkylaryl, alkylheteroaryl or C(O)Ot-Bu, comprising
(a) reacting a compound having the structure:

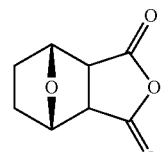

with a compound having the structure:

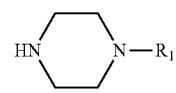

in the presence of a first organic solvent under conditions sufficient to produce the compound,
wherein the first organic solvent is a substituted benzene.

In one embodiment of the above process, $R_1$ is H, methyl, ethyl, hydroxyethyl, benzyl or tert-butyloxycarbonyl.

In one embodiment of the above process, $R_1$ is methyl.

The present invention provides a process for producing the compound having the structure:

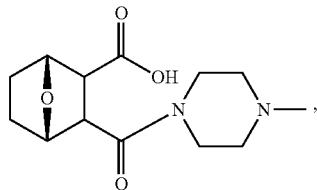 [SMILES: CN1CCN(C(=O)C2C(C(=O)O)[C@H]3CC[C@@H]2O3)CC1]

comprising
(a) reacting a compound having the structure:

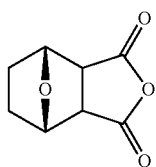

with a compound having the structure:

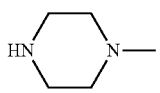

in the presence of a first organic solvent under conditions sufficient to produce the compound,
wherein the first organic solvent is a substituted benzene.

In some embodiments, a process for producing the compound having the structure:

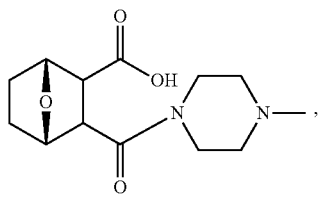 [SMILES: CN1CCN(C(=O)C2C(C(=O)O)[C@H]3CC[C@@H]2O3)CC1]

comprising
(a) reacting a compound having the structure:

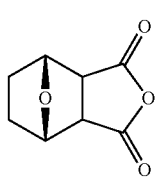

with a compound having the structure:

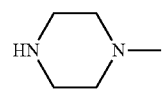

in the presence of a first organic solvent to produce the compound,
wherein the first organic solvent is a substituted benzene.

In some embodiments, a process for producing the compound having the structure:

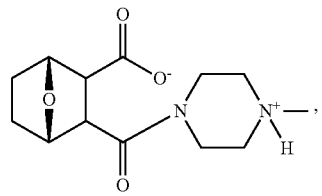 [SMILES: C[NH+]1CCN(C(=O)C2C(C(=O)[O-])[C@H]3CC[C@@H]2O3)CC1]

comprising

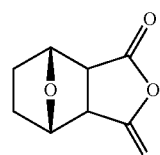

(a) reacting a compound having the structure:
with a compound having the structure:

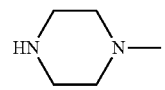

in the presence of a first organic solvent under conditions sufficient to produce the compound,
wherein the first organic solvent is a substituted benzene.

In some embodiments, a process for producing the compound having the structure:

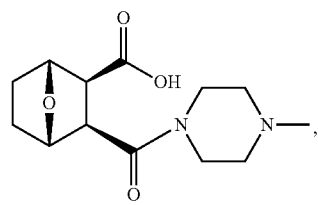 [SMILES: CN1CCN(C(=O)[C@@H]2[C@H](C(=O)O)[C@H]3CC[C@@H]2O3)CC1]

comprising
(a) reacting a compound having the structure:

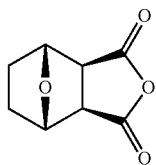 [SMILES: O=C1OC(=O)[C@H]2[C@@H]1[C@@H]1CC[C@H]2O1]

with a compound having the structure:

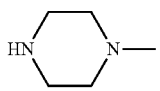

in the presence of a first organic solvent under conditions sufficient to produce the compound,
wherein the first organic solvent is a substituted benzene.

In some embodiments, the process wherein the compound having the structure:

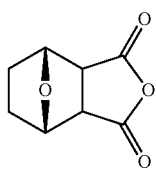

is initially added to an amount of the first organic solvent and the compound having the structure

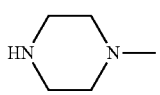

is subsequently added to the solution of the compound having the structure:

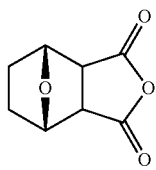

in the first organic solvent.

In some embodiments, the process wherein the compound having the structure:

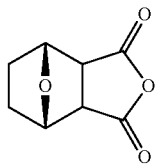

is dissolved or partially dissolved in the first organic solvent.

In some embodiments, the process wherein the compound having the structure:

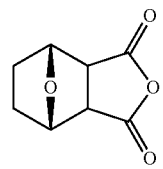 [SMILES: O=C1OC(=O)C2C1[C@@H]1CC[C@H]2O1]

is dissolved or partially dissolved in the first organic solvent prior to addition of the compound having the structure

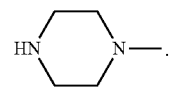.

In some embodiments, the process further comprising:
(b) filtering the reaction mixture of step (a) to obtain filtered solids.
In some embodiments, the process further comprising:
(c) washing the filtered solids produced in step (b) with an amount of the first organic solvent and an amount of a second organic solvent.
In some embodiments, the process further comprising:
(d) drying the washed solids produced in step (c) under vacuum.
In some embodiments, the process wherein the washed solids are dried under vacuum for 20-25 hours.
In some embodiments, the process wherein the washed solids are dried under vacuum at 70-90° C.
In some embodiments, the process wherein the second organic solvent is acetone.
In some embodiments, the process wherein the first organic solvent is a substituted benzene solvent.
In some embodiments, the process wherein the first organic solvent is isopropylbenzene (or cumene).
In some embodiments, the process wherein the first organic solvent is 1,3,5-trimethylbenzene, toluene, ethylbenzene, chlorobenzene, anisole, m-xylene or p-xylene.
In some embodiments, the process wherein the reaction is carried out at a temperature of 80-100° C.
In some embodiments, the process wherein the reaction is carried out at a temperature of 85-98° C.
In some embodiments, the process wherein the reaction is stirred for 15-25 hours.
In some embodiments, the process wherein the reaction is stirred for 18-23 hours.
In some embodiments, the process wherein the molar ratio of the 1-methylpiperazine to the norcantharidin is from 2:1 to 5:1
In some embodiments, the process wherein the molar ratio of the 1-methylpiperazine to the norcantharidin is 3:1.
In some embodiments, the process wherein the compound is isolated in >90% yield.
In some embodiments, the process wherein the compound is isolated in >95% yield.
In some embodiments, the process wherein the isolated compound has a purity >95%.
In some embodiments, the process wherein the isolated compound has a purity >97%.
In some embodiments, the process wherein the isolated compound has a purity >99%.
In some embodiments, the process wherein the isolated compound contains less than 5000 ppm of the first organic solvent.

In some embodiments, the process wherein the isolated compound contains less than 5000 ppm of the second organic solvent.

The present invention also provides a process for producing the compound having the structure:

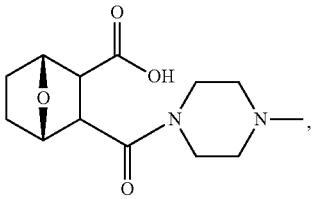 [SMILES: CN1CCN(C(=O)C2C(C(=O)O)[C@H]3CC[C@@H]2O3)CC1]

comprising (a) adding a compound having the structure:

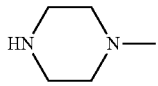

to a solution of a compound having the structure:

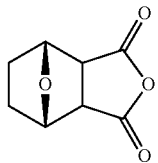

in isopropylbenzene;

(b) filtering the mixture of step (a) to obtain filtered solids;

(c) washing the filtered solids produced in step (b) with isopropylbenzene and acetone; and (d) drying the washed solids produced in step (b) under vacuum.

The present invention also provides a process for producing the compound having the structure:

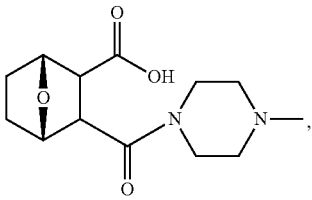 [SMILES: CN1CCN(C(=O)C2C(C(=O)O)[C@H]3CC[C@@H]2O3)CC1]

comprising (a) adding a compound having the structure:

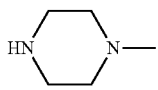

to a solution of a compound having the structure:

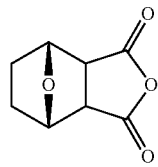 [SMILES: O=C1OC(=O)C2C1[C@@H]1CC[C@H]2O1]

in isopropylbenzene and stirring the solution for 16 to 24 hours at a temperature of 85 to 100° C.;

(b) filtering the mixture of step (a) to obtain filtered solids;

(c) washing the filtered solids produced in step (b) with isopropylbenzene and acetone; and (d) drying the washed solids produced in step (c) under vacuum.

The present reaction occurs under reaction conditions sufficient to produce the compound LB100. Such conditions, e.g. temperature, time, molarity, etc. may be varied by one of ordinary skill in the art based on the methods and protocols described herein. However, the use of cumene as solvent reduces the steps of production, simplifies purification and minimizes the residual solvent. The applicants have also found that use of cumene improves the yield and purity of the isolated LB100.

The process described herein is advantageous in that it avoids the need for using hazardous solvents such as benzene, which is not particularly desirable for industrial implementation due to the hazards associated with such solvent. Exposure to low concentrations of benzene vapour or to the liquid which has penetrated the skin may cause dizziness, lightheadedness, headache, loss of appetite and stomach upset. Exposure can also irritate the nose and throat. High exposures to benzene may cause irregularities in the heart beat which can lead to death. Benzene is a carcinogen.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Each embodiment disclosed herein is contemplated as being applicable to each of the other disclosed embodiments. Thus, all combinations of the various elements described herein are within the scope of the invention.

Each embodiment of the methods disclosed herein is contemplated as being applicable to the compound where R1 is other than methyl. Thus, all combinations of the various methods described herein where $R_1$ is other than methyl are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

A stock solution of anhydrous sodium carbonate ($Na_2CO_3$) in $D_2O$ containing TSP was prepared by dissolving 59.7 mg of Na2CO3 in 1 mL of $D_2O$ containing TSP. 100 μL of this stock solution was diluted with 900 μL of $D_2O$ containing TSP. 26.6 mg of LB100 was dissolved in this solution. The pH of this solution was approximately 8.1, tested using pH paper. $^1H$, $^{13}C$, DEPT-135, COSY, HSQC and HMBC spectra of this solution were acquired. A solvent blank was prepared from 100 μL of the stock solution, diluted with 900 μL of $D_2O$ containing TSP. The pH of this solution was approximately 10, using pH paper. $^1H$ and $^{13}C$ spectra of this solvent blank were acquired.

All spectra were acquired at ambient temperature on a JEOL ECX-400 NMR spectrometer operating at 400 MHz for $^1H$ and 100 MHz for $^{13}C$. The resulting FIDs were transferred to a PC and processed using NUTS NMR processing software from Acorn NMR Inc. Chemical shifts were referenced to TSP, 0 ppm.

Norcatharidin is available from a variety of suppliers, including Sigma-Aldrich (St. Louis, USA), Catalog No. N8784. 1-Methylpiperazine is available from a variety of suppliers, including Sigma-Aldrich (St. Louis, USA), Catalog No. 130001. Each of the above may be used with or without further purification.

The progress of the reaction can be monitored using any suitable method, which can include, for example, chromatographic methods such as, e.g., high performance liquid chromatography (HPLC), thin layer chromatography (TLC), and the like. The compound of formula can be optionally purified by any conventional techniques well known in the art.

Example 1

Reaction in Toluene

Norcantharidin (16.8 g, 0.1 mol) and N-methylpiperaz ne (30.0 g, 0.3 mol) were added to anhydrous toluene (100 mL) and heated at 90° C. overnight under nitrogen. The reaction mixture was cooled to room temperature where the solids were isolated by filtration. The solids were washed with anhydrous toluene (50 mL) and dried in air. The solids were off-white. Yield was 24.6 g (92%, Lot# 573-11-01-01C). See Table 1 for the residual solvent results. The synthesis step to make crude LB-100 was initially determined to be appropriate for scale-up manufacture of the crude product with no further development. The residual solvent toluene was to be removed with the incorporation of a recrystallization procedure.

In order to insert a clarification step to remove insoluble impurities as well as to purify the crude material, development was conducted to determine a LB-100 recrystallization procedure. The following experiments used crude LB-100 produce in Example 1.

Example 2

Methanol Trituration

The crude solids (5 g) were taken up in methanol (20 mL) and heated at reflux for two minutes. The slurry was cooled to room temperature and the solids were isolated by filtration. The solids were washed with methanol (20 mL) and dried at 80° C., under vacuum, to afford 4.7 g (94%, Lot# 573-11-01-03). See Table 1 for the residual solvent results.

This short-term exposure of the crude material to methanol afforded a good yield, however the material did not dissolve at this concentration (4 mL/g). In a different experiment, the crude solids were suspended in more dilute conditions in refluxing methanol (20 mL/g) for several hours to achieve a solution. A solid for this experiment, however, was never noted until the solution was concentrated to a residue (in vacuum). See Table 1 for the residual solvent results.

Example 3

Toluene Trituration

The crude solids (1 g) were digested in hot toluene (15 mL) for 1 hour. The slurry was cooled to room temperature and the solids were isolated by filtration. The solids were dried at 80° C., under vacuum, to afford 0.86 g (86%). This experiment demonstrated low solubility of the material in toluene. Based on this observation, in the following experiment toluene was further tried as an anti-solvent.

Example 4

Water and Toluene/2-Propanol Recrystallization

The crude solids (1 g) were dissolved in water (2 at ambient temperature. Toluene (10 mL) was added to the solution and the mixture was heated to reflux.

Using a Dean-Stark trap, water was removed and an oily residue formed in the bottom of the flask. The toluene was decanted off and the residue was air-dried. The residue was re-dissolved in water (2 mL) and 2-propanol (20 mL) was charged. The resulting slurry was stirred at room temperature overnight, and the solids were isolated by filtration. The solids were washed with 2-propanol (to cover the solids) and air dried to afford 0.53 g product (53%).

In this experiment the oiling of the product in toluene and forming a residue on the bottom of the flask showed that toluene is not a desired crystallization solvent. Fortunately, the 2-propanol had afforded a filterable solid. This solvent was used for further recrystallization studies.

Example 5

Water and 2-Propanol Recrystallization without Azeotrope Removal of Water

The crude solids (0.5 g) were dissolved in water (1 mL) and 2-propanol (5 mL) was charged. The resulting slurry was stirred at room temperature for 1 hour, and then isolated by filtration. The solids were washed with 2-propanol (to cover the solids) and air dried to afford 0.1 g (20% recovery yield).

This experiment demonstrated that a recrystallization from water and 2-propanol, although affording solids, did not give a reasonable yield. The compound has a high solubility in water, and therefore necessitating water removal after the clarification step.

Example 6

Water and 2-Propanol Recrystallization with Azeotrope Removal of Water

The crude solids (1 g) were dissolved in water (2 mL) and 2-propanol (20 mL) was charged. A slurry resulted and the water was azeotropically removed using 2-propanol under atmospheric distillation. The slurry was stirred at room temperature overnight and then the solids were isolated by filtration. The product was washed with 2-propanol (4 mL in 2 portions) and air dried to afford 0.7 g (70%).

This crystallization gave a higher yield. Some in-process testing for residual solvents, however, indicated that the solid may contain high levels of 2-propanol (2% propanol, above ICH limits). To reduce the residual solvent level, acetone was evaluated as a crystallization solvent.

Example 7

Water and Acetone Recrystallizations

A) Addition of Water Solution to Acetone

The solids (1 g) were dissolved in water (1.7 mL) at ambient temperature. The resulting solution was added drop-wise to acetone (16.6 mL) under stirring. Some solids formed, but much of the mixture was a sticky residue on the flask walls.

This residue hardened over time and partially released from the walls. The solids were isolated, washed with acetone (2 mL) and dried under vacuum at 80° C. to yield 0.86 g (86%) as a white solid. See Table 1 for the residual solvent result.

B) Addition of Acetone to Water Solution

The solids (1 g) were dissolved in water (1.7 mL) at ambient temperature. Acetone (16.6 mL was added to the resulting solution by drop-wise addition. Mostly an oil formed and this solidified over time to result in a mixable slurry. The solids were isolated, washed with acetone (2 mL) and dried at 80° C., under vacuum. The white solids were 0.92 g (92%, Lot# 573-11-01-14). See Table 1 for the residual solvent result.

C) Scale-up of the Recrystallization from Acetone/Water

Both experiments were scaled-up to 10-gram scale, however, showed they that the yield and purity of solids obtained were not consistent (. Even though the residual solvents result from these experiments met the limits, the inconsistent yields and the oiling of the solids caused this work to be abandoned. A new treatment, using water only, was investigated due to the difficulty to obtain a true solid using acetone.

Example 8

Water Treatment of Solids to Reduce Residual Solvent Levels to ICH Guidelines

The solids (0.5 g) were dissolved in water (425 µL) and the resulting solution was concentrated (vacuum, 80° C. bath) to a foam. The material was tested for residual solvents and the result met the ICH limit (for details see Table 1).

TABLE 1

| Example | Residual Solvents | Comments |
|---|---|---|
| 1 | 154 ppm (MeOH) 1890 ppm (toluene) | Toluene levels are ~2 times over the ICH limit. |
| 2 | 4678 ppm (MeOH) | MeOH level is above ICH limit. |
| 2 | 159 ppm (MeOH) 1792 ppm (toluene) | Toluene levels are ~2 times over the ICH limit. |
| 7A | 4748 ppm (acetone) | Acetone level is near ICH limit. |
| 7B | 3760 ppm (acetone) | Acetone level is under ICH limit, indicating material may not retain acetone |

TABLE 1-continued

| Example | Residual Solvents | Comments |
|---|---|---|
| 8 | 2548 ppm (1-propanol) 711 ppm (acetone) | Solvent levels below ICH limit. |

Example 9

Scale-up of the Process to Make LS-100 using Water

Norcantharidin (76.8 g, 0.457 mol) and N-methylpiperazine (137.2 g, 1.370 mol) were added to anhydrous toluene (450 mL) and heated at 90° C. under nitrogen overnight. The reaction mixture was cooled to room temperature where the solids were isolated by filtration. The solids were washed with anhydrous toluene (250 mL in 2 portions) and dried in air for 2 hours then dried at 80° C., under vacuum, overnight. The solids were off-white. Yield was 106.6 g (87%).

The crude material (106.5 g) was dissolved in water (200 mL) and the solution was clarified through a 10 µm filter. The solution was diluted with 2-propanol (500 mL) and concentrated (vacuum, 40° C. bath) until 500 mL of distillate was collected. Additional 2-propanol (4 portions of 500 mL each) was used followed by the azeotropic distillation (vacuum, 40° C. bath) to result in a white slurry. The slurry was diluted with 2-propanol (250 mL) and after removing another 200 mL of distillate (vacuum, 40° C. bath), the suspension was stirred overnight. The solids were isolated by filtration. The solids were washed with 2-propanol (200 mL in 2 portions) and dried under vacuum at 80° C. overnight. The solids were off-white. Yield was 98.0 g (92%).

The solids (96.5 g) were dissolved in water (190 mL) and the solution was diluted with 2-propanol (500 mL). The mixture was concentrated on a rotary evaporator (vacuum, 40° C. bath) until 500 mL of distillate was collected. The concentrated solution was diluted with 2-propanol (500 mL) followed by the azeotropic distillation (vacuum, 40° C. bath) to collect 500 mL of distillate. The solution was diluted with 2-propanol (500 mL) and after removing another 30 mL of distillate (vacuum, 40° C. bath), the mixture became turbid. After mixing in an ice/water bath for 1 hour the solids were isolated by filtration. The solids were washed with 2-propanol (200 mL in 2 portions) and dried at 80° C., under vacuum, overnight. The solids were off-white. Yield was 84.7 g (88%). The solids contained 2.0% 2-propanol and consequently it was necessary to be treated further using water. A portion of the recrystallized solids (67.8 g) were charged to a 2-L rotary evaporator flask. Water (57.6 mL) was charged and the resulting slurry was heated (80° C.) vacuum on the rotary evaporator. A clear solution resulted. This solution was concentrated to a residue (vacuum, 80° C. bath). The residue hardened and was transferred to a tray and dried at 80° C., under vacuum. The solids (Batch 1, 62.3 grams, 92% recovery) were packaged. The testing results are shown in Table 2.

Another batch of LB-100 was produced under similar conditions with the exception that one crystallization instead of two was conducted using water and 2-propanol. The solids (Batch 2, 1.4160 kg, 72% overall yield) were packaged. The testing results are shown in Table 2.

TABLE 2

| Test | Specification | Batch 1 | Batch 2 |
|---|---|---|---|
| HPLC (a/a %) | Prefer > 97 | 98.86 | 99.37 |
| LS-MS (mass %) | Prefer > 95 | 76.86 | 79.93 |
| Elemental (%) | | C = 56.69 | C = 56.64 |
| | C = 58.19 | H = 7.35 | H = 7.50 |
| | H = 7.51 | N = 9.36 | N = 10.15 |
| | N = 10.44 | | |
| XRPD | — | No Crystalline Pattern | — |
| DSC | — | Onset Temp. = 209.76° C. | — |
| TGA | — | 9.457% between 26.42 and 200.00° C. | — |

Example 10

Purification Screening

A digestion of LB100 in selected organic solvents (methanol, 2-propanol and toluene) were attempted to either reduce the toluene level or to increase the purity of the product. The experiments are shown in Table 3. All samples in this set of experiments showed high levels of toluene as shown in Table 3.

TABLE 3

| Amount Charged | | 0.497 g | 0.496 g | 0.254 g | 1.046 g | 10.091 g |
|---|---|---|---|---|---|---|
| Solvent added | | MeOH (5 mL) | 2-propanol (5 mL) | 2-propanol (2.5 mL) | Toluene (10 mL) | Toluene (10 mL) |
| Slurry Conditions | | Heat to apparent reflux then slowly cool to rt | Heat to apparent reflux then slowly cool to rt | Heat to apparent reflux then slowly cool to rt | Room temperature slurry | Heat to apparent reflux then slowly cool to rt |
| New weight | | 0.325 g | 0.384 g | 0.095 g | 0.889 g | 0.938 g |
| Recovery | | 65.4% | 77.4% | 37.4% | 85.0% | 86.0% |
| HPLC (a/a %) | Prefer >97 | 99.52 | 99.45 | 99.51 | 99.48 | 99.59 |
| LS-MS (Mass %) | Prefer >95 | 96.01 | 95.51 | 91.97 | 88.86 | 90.80 |
| Residual Solvents | Toluene ≤890 | 1421 | 4528 | 8309 | 7810 | 17815 |
| | MeOH ≤3,000 | — | — | — | — | — |
| | 2-Propanol ≤5,000 | 394 | 430 | 632 | 1242 | 640 |

Example 11

Solvent Screen for Reaction

Screening was conducted for a reaction solvent as shown in the following table:

TABLE 4

| Solvent | MTBE | 2-MeHTF | 2-Methylpiperazine | Cumene | Anisole |
|---|---|---|---|---|---|
| Amount Charged | 10.0 g | 10.0 g | 10.0 g | 10.0 g | 10.0 g |
| Reaction Temp. (° C.) | 55 | 77 | 90 | 90 | 90 |
| Crude Yield | — | — | — | 13.4 g 84% | 12.3 g 84% |
| HPLC (a/a %) | 99.30 | 99.55 | No solids isolated | 99.51 | 99.49 |
| LS-MS (Mass %) | 85.71 | 94.75 | No solids isolated | 97.26 | 100.00 |

MTBE, cumene and anisole are ICH Class III solvents, while 2-methyltetrahydrofuran and 2-methylpiperazine are not classified. It was desirable to use a Class III solvent. In addition, the reaction temperature is critical in order that the reaction go to completion, and a high boiling solvent, therefore, is desired. The starting material is more soluble in cumene than anisole so therefore cumene was chosen for further experiments.

Since cumene is a high boiling solvent (152-154° C.), a lower boiling solvent was considered to work-up the reaction mixture. The starting material was found to be soluble in acetone and the boiling point of this solvent is 56° C. making this solvent a good choice. Several experiments were conducted to show that acetone is good at removing 1-3% of the starting material, but not sufficient enough to remove trapped or excessive amounts (>3%) of starting material. The conclusion was that the reaction must be conducted in cumene at 90° C. to achieve high yields of product and the acetone should be used to remove as much of the starting materials as possible and to displace the higher boiling cumene.

Example 12

Cumene as Solvent

To a 250-mL 3-necked flask equipped with a heating mantle, agitator, nitrogen sweep, thermometer and condensing column was charged cumene (96 mL), norcantharidrin (12.0 g, 0.0714 mol) and cumene (27 mL). The resulting slurry was heated to 110° C. where a solution formed after 40 minutes of stirring at 110° C. The solution was cooled and crystals were noted to form at 73.6° C. At 30° C., N-methylpiperazine (23.7 mL, 0.214 mol, 3.0 mol eq.) was added.

After the initial exotherm ($T_{max}$=46.5° C.), the resulting solution was heated to approximately 90° C. The mixture was stirred at approximately 90° C. for 16 hours.

The slurry was cooled to ambient temperature and the solids were isolated. The solids were washed with cumene (20.0 mL), acetone (3×20.0 mL) and dried at 80° C. and under vacuum (28 to 30 in. Hg). The net solid weight was 17.6 g (91.9% yield). The testing results are shown below:

TABLE 5

| Test | Specification | Batch 1 |
|---|---|---|
| HPLC (a/a %) | Prefer > 97 | 97.31 |
| LS-MS (mass %) | Prefer > 95 | 97.48 |
| Elemental (%) | C = 58.19 | C = 58.33 |
|  | H = 7.51 | H = 7.75 |
|  | N = 10.44 | N = 10.60 |
| Residual Solvent (ppm) | Acetone ≤ 5,000 | 19 |
|  | Cumene ≤ 5,000 | 1397 |
| XRPD | — | Crystalline Pattern |
| DSC | — | Onset Temp. = 230.27° C. |

Example 13

Preparation of LB100 with Cumene as Solvent

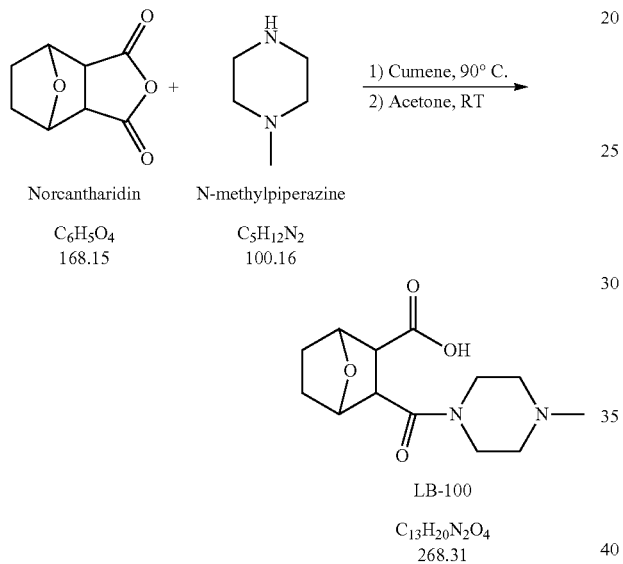

To a 22-L 3-necked flask equipped with a heating mantle, agitator, nitrogen sweep, thermometer and condenser was charged cumene (6.2028 kg), norcantharidin (0.9027 kg, 5.368 mol), cumene (1.5549 kg), and N-methylpiperazine (1.6067 kg, 16.041 mol, 3.0 mol eq.). A solution resulted and this was mixed while heating to approximately 90° C. The mixture was stirred for 21 hours in the range of 85.1 to 97.1° C.

The slurry was cooled to ambient temperature and the solids were isolated. The solids were washed with cumene (1.1703 kg), acetone (1.1281 kg, 1.1617 kg, and 1.1850 kg) and dried at 80° C. and under vacuum (28 to 30 in Hg) for a total of 22 hours and 25 minutes. The packaged solid weight was 1.3743 kg (95.4% yield).

Example 14

Cumene as Solvent Scale-Up

Figure 3:
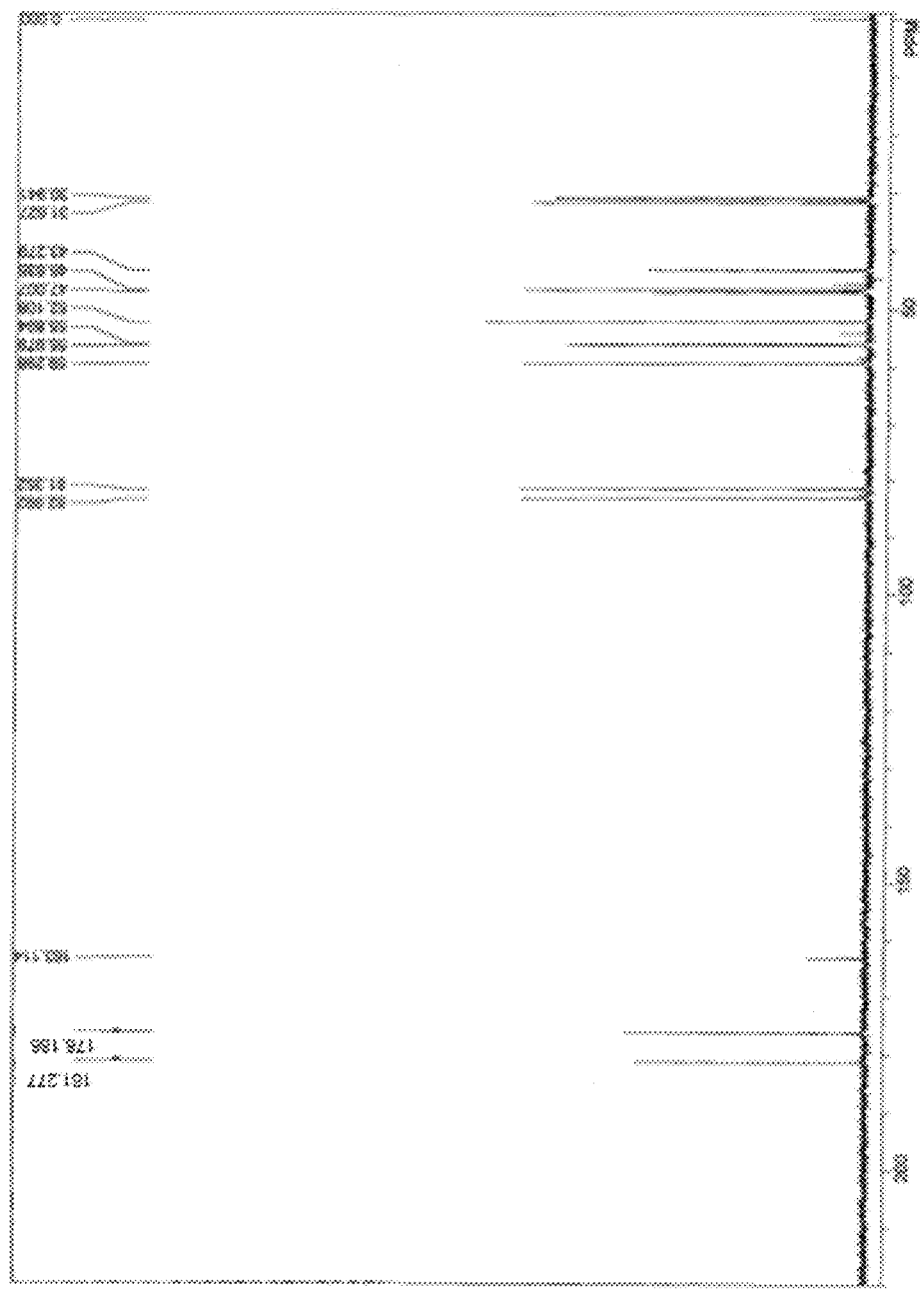

To a 2-L 3-necked flask equipped with a heating mantle, agitator, nitrogen sweep, thermometer and condenser was charged cumene (640 mL), norcantharidrin (80.0 g, 0.476 mol) and cumene (160 mL). At room temperature, N-methylpiperazine (158.2 mL, 1.426 mol, 3.0 mol eq.) was added. After the initial exotherm ($T_{max}$=46.0° C.), the resulting solution was heated to approximately 90° C. The mixture was stirred for 16 hours at approximately 90° C. The slurry was cooled to ambient temperature and the solids were isolated. The solids were washed with cumene (130.0 mL), acetone (3×130.0 mL) and dried at 80° C. and under vacuum (28 to 30 in Hg). The net solid weight was 121.0 g (94.8% yield). The in-process testing results are shown in Table 6. Spectroscopic data for the product is shown in FIGS. 2-3.

TABLE 6

| Test | Specification | Batch 1 |
|---|---|---|
| HPLC (a/a %) | Prefer > 97 | 99.40 |
| LS-MS (mass %) | Prefer > 95 | 96.05 |
| Elemental (%) | C = 58.19 | C = 58.26 |
|  | H = 7.51 | H = 7.50 |
|  | N = 10.44 | N = 10.62 |
| Residual Solvent (ppm) | Acetone ≤ 5,000 | 14 |
|  | Cumene ≤ 5,000 | 1435 |

Example 15

Additional Substrates

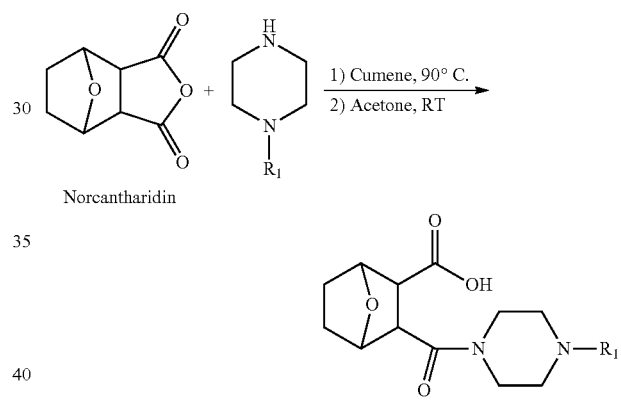

In some embodiments of the above scheme, $R_1$ is s H, methyl, ethyl, hydroxyethyl, benzyl or tert-butyloxycarbonyl.

To a 250-mL 3-necked flask equipped with a heating mantle, agitator, nitrogen sweep, thermometer and condensing column is charged cumene (96 mL), norcantharidrin (12.0 g, 0.0714 mol) and cumene (27 mL). The resulting slurry is heated to 110° C. where a solution forms after 40 minutes of stirring at 110° C. The solution is cooled and at 30° C., the appropriate N-subsitutued piperazine (23.7 mL, 0.214 mol, 3.0 mol eq.) isadded. After the initial exotherm, the resulting solution is heated to approximately 90° C. The mixture is stirred at approximately 90° C. for 16 hours.

The slurry is cooled to ambient temperature and the solids are isolated. The solids are washed with cumene (20.0 mL), acetone (3×20.0 mL) and are dried at 80° C. and under vacuum (28 to 30 in. Hg). The yield is >90%.

To a 3-necked flask equipped with a heating mantle, agitator, nitrogen sweep, thermometer and condenser is charged cumene (6.2028 kg), norcantharidin (0.9027 kg, 5.368 mol), cumene (1.5549 kg), and the appropriate N-subsitutued piperazine (3.0 mol eq. relative to norcantharidin). A solution results and is mixed while heating to approximately 90° C. The mixture is stirred for 21 hours in the range of 85.1 to 97.1° C.

The slurry is cooled to ambient temperature and the solids are isolated. The solids are washed with cumene (1.1703 kg), acetone (1.1281 kg, 1.1617 kg, and 1.1850 kg) and are dried at 80° C. and under vacuum (28 to 30 in. Hg). The yield is >90%.

Discussion

Inhibition of PP2A interferes with multiple aspects of the DNA damage repair (DDR) mechanisms and with exit from mitosis. These mechanisms sensitize cancer cells to cancer treatments that cause acute DNA injury. Compound LB100 (see U.S. Pat. No. 7,998,957 B2) has anti-cancer activity when used alone (Lu el al. 2009a) and significantly potentiates in vivo, without observable increase in toxicity, the anti-tumor activity of standard cytotoxic anti-cancer drugs including temozolomide (Lu et al. 2009b, Martiniova et al. 2010), doxorubicin (Zhang et al. 2010), and docetaxel. LB100 was recently approved for Phase I clinical evaluation alone and in combination with docetaxel and is in clinical trial.

U.S. Pat. No. 7,998,957 describes a synthesis of LB100. However, the solvent benzene is well known to those of ordinary skill in the art as toxic and unsuitable for large scale synthesis. The methods described herein employ less toxic solvents and provide LB100 with improved yield, improved purity and decreased residual solvent.

REFERENCES

Arnold H K, Sears R C. A tumor suppressor role for PP2A-B56alpha through negative regulation of c-Myc and other key oncoproteins. Cancer Metastasis Rev 2008; 27:147-58.

Chen W, et al. Identification of specific PP2A complexes involved in human cell transformation. Cancer Cell 2004; 5:127-36.

Chung V, M. A., Phase I study of LB-100 with docetaxel in solid tumors. 2013: ClinicalTrials.gov.

Efferth, T., et al., Activity of drugs from traditional Chinese medicine toward sensitive and MDR1- or MRP1-overexpressing multidrug-resistant human CCRF-CEM leukemia cells. Blood Cells Mol Dis, 2002. 28(2): p. 160-8.

Gwinn D, Sweet-Cordero E A. The Phosphatase PP2A Links Glutamine to the Tumor Suppressor p53. Mol Cell 2013; 50:157-8.

Hart M E, et al. Modified norcantharidins; synthesis, protein phosphatases 1 and 2A inhibition, and anticancer activity. Bioorg Med Chem Lett 2004;14:1969-73.

Junttila M R, et al. CIP2A inhibits PP2A in human malignancies. Cell 2007;130:51-62.

Kalev, P. Loss of PPP2R2A inhibits homologous recombination DNA repair and predicts tumor sensitivity to PARP inhibition. Cancer Res. 2012 Dec. 15;72(24):6414-24.

Li W, et al. Cantharidin, a potent and selective PP2A inhibitor, induces an oxidative stress-independent growth inhibition of pancreatic cancer cells through G2/M cell-cycle arrest and apoptosis. Cancer Sci 2010;101:1226-33.

Liu D, Chen Z. The effects of cantharidin and cantharidin derivates on tumour cells. Anticancer Agents Med Chem 2009;9:392-6.

Lu, J. et al (2009a) J Neurosurgery Vol. 113, No. 2, Pages 225-233.

Lu, J. et al (2009b) PNAS 106(28), 11697-11702.

Martin ova, L., et al., Pharmacologic modulation of serine/threonine phosphorylation highly sensitizes PHEO in a MPC cell and mouse model to conventional chemotherapy. PLoS One, 2011. 6(2): p. e14678.

McCluskey A, et al. Anhydride modified cantharidin analogues: synthesis, inhibition of protein phosphatases 1 and 2A and anticancer activity. Bioorg Med Chem Lett 2000; 10:1687-90.

Mumby M. PP2A: unveiling a reluctant tumor suppressor. Cell 2007;130:21-4.

Reid M A, et al. The B55alpha Subunit of PP2A Drives a p53-Dependent Metabolic Adaptation to Glutamine Deprivation. Mol Cell 2013;50:200-11.

Suganuma M, et al. Okadaic acid: an additional non-phorbol-12-tetradecanoate-13-acetate-type tumor promoter. Proc Natl Acad Sci U S A 1988;85:1768-71.

Wei, D., et al., Inhibition of protein phosphatase 2A radiosensitizes pancreatic cancers by modulating CDC25C/CDK1 and homologous recombination repair. Clin Cancer Res, 2013. 19(16): p. 4422-32.

Zhang, C., et al., A synthetic cantharidin analog for the enhancement of doxorubicin suppression of stem cell-derived aggressive sarcoma. Biomaterials, 2010. 31(36): p. 9535-43.

What is claimed is:

1. A process for producing the compound having the structure:

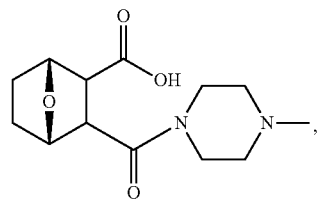

or a salt or zwitterion thereof,
comprising:
(a) adding a compound having the structure:

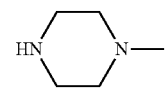

to a solution of a compound having the structure:

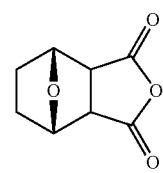 [SMILES: O=C1OC(=O)C2C1[C@@H]1CC[C@H]2O1]

in isopropylbenzene;
(b) filtering the mixture of step (a) to obtain filtered solids;
(c) washing the filtered solids produced in step (b) with isopropylbenzene and acetone; and
(d) drying the washed solids produced in step (b) under vacuum.

2. A process for producing the compound having the structure:

or a salt or zwitterion thereof,
comprising:
(a) adding a compound having the structure:

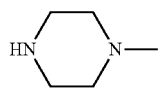

to a solution of a compound having the structure:

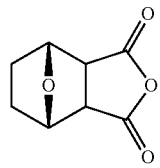 [SMILES: O=C1OC(=O)C2C1[C@@H]1CC[C@H]2O1]

in isopropylbenzene and stirring the solution for 16 to 24 hours at a temperature of 85 to 100° C.;
(b) filtering the mixture of step (a) to obtain filtered solids;
(c) washing the filtered solids produced in step (b) with isopropylbenzene and acetone; and
(d) drying the washed solids produced in step (c) under vacuum.

* * * * *